(12) United States Patent
Myers et al.

(10) Patent No.: US 8,603,406 B2
(45) Date of Patent: Dec. 10, 2013

(54) FOR DRYING REGENERATED CATALYST IN ROUTE TO A PROPANE DEHYDROGENATION REACTOR

(75) Inventors: David N. Myers, Hoffman Estates, IL (US); Daniel N. Myers, Arlington Heights, IL (US); Paolo Palmas, Des Plaines, IL (US); Laura E. Leonard, Western Springs, IL (US); Wolfgang A. Spieker, Glenview, IL (US)

(73) Assignee: UOP LLC, Des Plaines, IL (US)

( * ) Notice: Subject to any disclaimer, the term of this patent is extended or adjusted under 35 U.S.C. 154(b) by 164 days.

(21) Appl. No.: 12/871,296

(22) Filed: Aug. 30, 2010

(65) Prior Publication Data
US 2012/0051981 A1    Mar. 1, 2012

(51) Int. Cl.
*B01J 23/90* (2006.01)
*B01J 19/00* (2006.01)
*B01J 8/00* (2006.01)
*B01J 8/02* (2006.01)
*B01J 8/18* (2006.01)
*B01J 35/02* (2006.01)
*B01J 29/70* (2006.01)
*F27B 15/00* (2006.01)
*F27B 15/08* (2006.01)
*F27B 15/14* (2006.01)
*F27B 15/16* (2006.01)

(52) U.S. Cl.
USPC ........... 422/223; 422/129; 422/139; 422/140; 422/141; 422/142; 422/143; 422/144; 422/145; 422/146; 422/147; 422/187; 422/211; 208/46

(58) Field of Classification Search
USPC ................. 422/129, 139–147, 211, 223, 187; 208/46, 146, 153, 163, 177, 208 R, 230, 208/235
See application file for complete search history.

(56) References Cited

U.S. PATENT DOCUMENTS

| | | | | |
|---|---|---|---|---|
| 4,033,726 A | * | 7/1977 | Pulak | 422/144 |
| 4,064,038 A | * | 12/1977 | Vermilion, Jr. | 208/120.01 |
| 5,059,305 A | * | 10/1991 | Sapre | 208/113 |
| 5,087,792 A | * | 2/1992 | Cottrell et al. | 585/661 |
| 6,162,402 A | * | 12/2000 | Lomas | 422/144 |
| 6,362,385 B1 | | 3/2002 | Iezzi et al. | |
| 7,235,706 B2 | | 6/2007 | Iezzi et al. | |
| 7,273,543 B2 | * | 9/2007 | Letzsch | 208/113 |
| 7,423,191 B2 | | 9/2008 | Senetar | |
| 2002/0183403 A1 | | 12/2002 | Huang | |
| 2008/0097134 A1 | | 4/2008 | Fridman et al. | |

(Continued)

FOREIGN PATENT DOCUMENTS

CN    1912065 A1    2/2007
RU    2214383 C1    10/2003

OTHER PUBLICATIONS

U.S. Appl. No. 12/871,277, filed Aug. 30, 2010, Myers et al.

*Primary Examiner* — Prem C Singh
*Assistant Examiner* — Natasha Young
(74) *Attorney, Agent, or Firm* — Arthur E Gooding

(57) ABSTRACT

An apparatus and process are presented for drying a catalyst in a reactor-regenerator system. The process includes a continuous operating system with catalyst circulating between a reactor and regenerator, and the catalyst is dried before returning the catalyst to the reactor. The process uses air that is split between the drying stage and the combustion stage without adding equipment outside of the regenerator, minimizing energy, capital cost, and space requirements.

18 Claims, 1 Drawing Sheet

(56) References Cited

U.S. PATENT DOCUMENTS

| | | |
|---|---|---|
| 2008/0161624 A1 | 7/2008 | Glover et al. |
| 2009/0012341 A1 | 1/2009 | Brophy et al. |
| 2009/0240094 A1 | 9/2009 | Crone et al. |
| 2009/0325783 A1 | 12/2009 | Myers |
| 2010/0105540 A1 | 4/2010 | Galliou |
| 2012/0053047 A1* | 3/2012 | Myers et al. .................. 502/56 |

* cited by examiner

FOR DRYING REGENERATED CATALYST IN ROUTE TO A PROPANE DEHYDROGENATION REACTOR

FIELD OF THE INVENTION

This invention relates to an apparatus and process in catalytic hydrocarbon processing. In particular, this invention relates to improving regenerators, and the process of regenerating catalyst.

BACKGROUND OF THE INVENTION

There are many processes that have been developed for converting hydrocarbon streams to more useful products. Many of these processes involve the use of catalysts, and many of the catalytic processes are continuously operated. The continuous operation of a catalytic process can involve a fluidized bed reactor, and a regenerator. The catalyst is used in the reactor, and is continuously drawn off as spent catalyst and passed to a regenerator. The regenerator regenerates the spent catalyst and recycles the catalyst back to the reactor.

One common process, as an example, is fluid catalytic cracking. The process is a conversion process to convert heavy hydrocarbons into lighter hydrocarbons. The reaction occurs through contact between the hydrocarbon stream of heavy hydrocarbons with catalyst particles. The particles eventually lose their activity, and need to be regenerated. The basic components of such a process includes a reactor, a catalyst stripper and a regenerator. The reaction takes place in the reactor, where the catalyst is eventually deactivated through the accumulation of coke on the catalyst particles. The catalyst is carried out of the reactor, where residual hydrocarbons are stripped from the catalyst, and the catalyst is passed to the regenerator, where the coke is burned off, and the catalyst is regenerated.

However, some processes using this basic structure may require additional steps to maintain the long term viability of the continuous process.

BRIEF SUMMARY OF THE INVENTION

The present invention is a regenerator design for a paraffin dehydrogenation reactor-regenerator system. The regenerator design includes a combustion chamber having a spent catalyst inlet, a combustion gas inlet, and an outlet. The regenerator further includes a drying chamber having an inlet in fluid communication with the combustion chamber outlet, where the catalyst and combustion flue gas separate and the catalyst settles to be contacted with a drying gas. The drying chamber includes a catalyst outlet and a drying gas inlet, wherein the catalyst outlet is in fluid communication with a stripping chamber catalyst inlet. The stripping chamber has a stripping gas inlet and a catalyst outlet in fluid communication with the reactor catalyst inlet.

In another embodiment, the regenerator design comprises an efficient stacking of the stripping chamber, drying chamber and combustion chamber. The combustion chamber has a spent catalyst inlet and a combustion gas inlet. The regenerated catalyst and combustion chamber flue gas pass to a separation chamber where the catalyst is separated from the flue gas. The catalyst is passed to the drying chamber positioned below the combustion chamber. A drying gas is passed to the drying chamber to remove water from the catalyst, and the moist gas is passed to the combustion chamber where the gas is used in the combustion of coke on the catalyst. The drying chamber has a catalyst outlet where the catalyst is passed to a stripping chamber. The stripping chamber has a stripping gas inlet, and the stripping gas after contacting the catalyst can be passed to the drying chamber, or can be passed to the separation chamber where the stripping gas will be passed out with the flue gas. The stripping chamber has a catalyst outlet where the catalyst can be returned to the reactor.

Other objects, advantages and applications of the present invention will become apparent to those skilled in the art from the following detailed description and drawings.

DETAILED DESCRIPTION OF THE INVENTION

Figure 2:
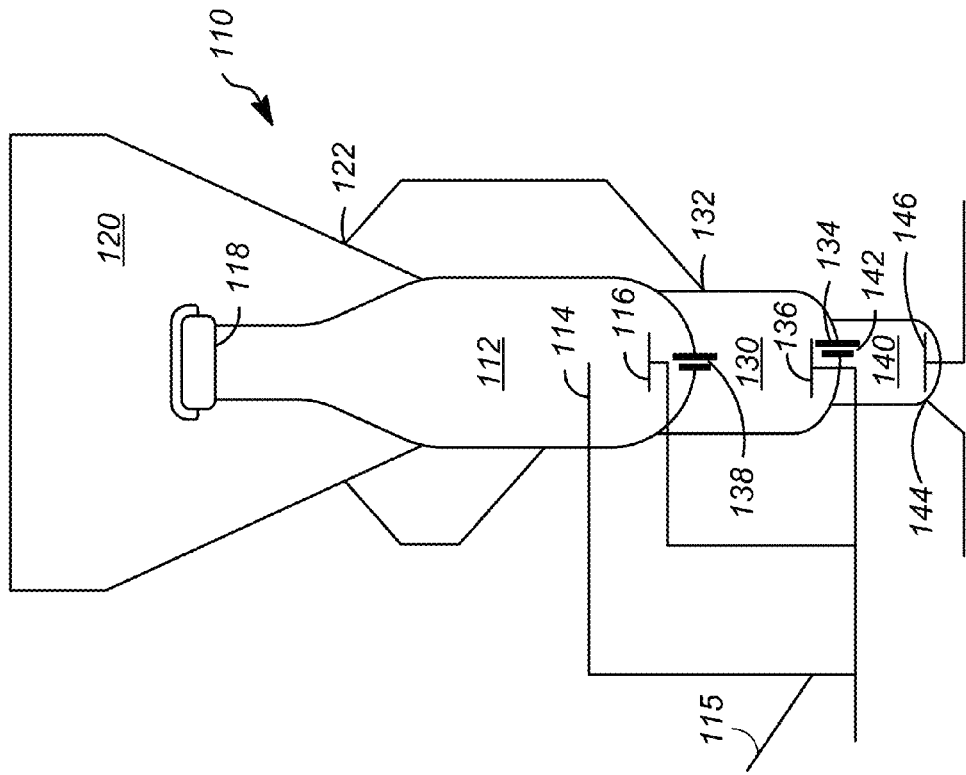
FIG. 2 is a second configuration for performing the catalyst drying.

Propylene is an important precursor to the plastic polypropylene. A process has been developed to produce on-purpose propylene from a propane rich feedstock. The process of the present invention involves the dehydrogenation of propane using a non-noble metal catalyst in a fluidized reactor-regenerator system. However, depending upon which catalyst type is chosen, sensitivity of the catalyst to water can be an issue, and the regeneration process produces some moisture that can be adsorbed onto the regenerated catalyst. The dehydrogenation process comprises passing a paraffinic hydrocarbon to a dehydrogenation reactor. In the reactor, a dehydrogenation catalyst is circulated between the reactor and a regenerator for a continuous process, wherein the catalyst undergoes deactivation while in the reactor during the dehydrogenation process, and is regenerated in a regenerator and returned to the reactor. In particular, the design of the present invention is aimed at the process of converting propane to propylene. In addition, the presence of oxygen and/or carbon monoxide affects the dehydrogenation process. The catalyst needs to have residual oxygen and/or carbon monoxide that is adsorbed on the catalyst during regeneration needs to be removed. Simple purging of the catalyst from the regenerator is often insufficient to remove enough of the residual water to return the catalyst to a state to achieve the desired performance.

The present invention represents an integrated catalyst regeneration and drying approach which is an improvement over a non-integrated approach where an additional drying vessel would be employed requiring additional complexity, and operation equipment and plot space. This invention reduces capital cost by avoiding the addition of a non-integrated dedicated drying system which would require catalyst handling and gas/catalyst separation equipment. The regenerated catalyst is contacted with a dry gas such as air or nitrogen to remove more than 90% of the water adsorbed by the catalyst in the regenerator, and preferably more than 99.9% of the water. The extent of drying is determined by the level of activity needed in the regenerated catalyst.

The present invention is intended to include any reactor design that incorporates a recirculation of the catalyst between a reactor and a regenerator, including a fluidized bed system, a fast fluidized bed system, a bubbling bed reactor system, or a counter-current flow system involving trays or packing.

One embodiment of the present invention is a process for drying regenerated catalyst in a continuous catalyst regeneration system. The process includes passing spent catalyst from a dehydrogenation reactor to a regenerator. The catalyst is regenerated through the combustion of coke deposits on the catalyst to return the catalyst to an active state. In a regenerator, the catalyst is subject to heating and an oxidizing gas. The combustion of the coke provides the heating of the catalyst. Additional fuel can be added to the regenerator to insure sufficient heating and combustion of the coke on the catalyst. The catalyst is carried out of the combustor style regenerator with the combustion gas effluent. The catalyst and combustion gas effluent are partially separated, and the regenerated catalyst settles in a dryer positioned at the outlet of the regenerator, forming a dense bed of catalyst in the dryer. Water is generated in the combustion process and adsorbed onto the catalyst. A drying gas is passed to the dryer and flows over the catalyst in a fluidized bed to remove adsorbed water. The fluidized bed can be a bubbling bed, or other fluidized bed wherein the catalyst is well mixed with the drying gas, and the catalyst flows through the bed as it is dried.

In another embodiment, the process further includes passing the dried catalyst to a stripping unit thereby creating a stripped and dried catalyst that is passed to the reactor. A stripping gas is passed to the stripping unit to remove residual oxygen on the catalyst. The stripping gas can be any inert gas, such as nitrogen, or other inert gas, or a mixture of inert gases.

Figure 1:
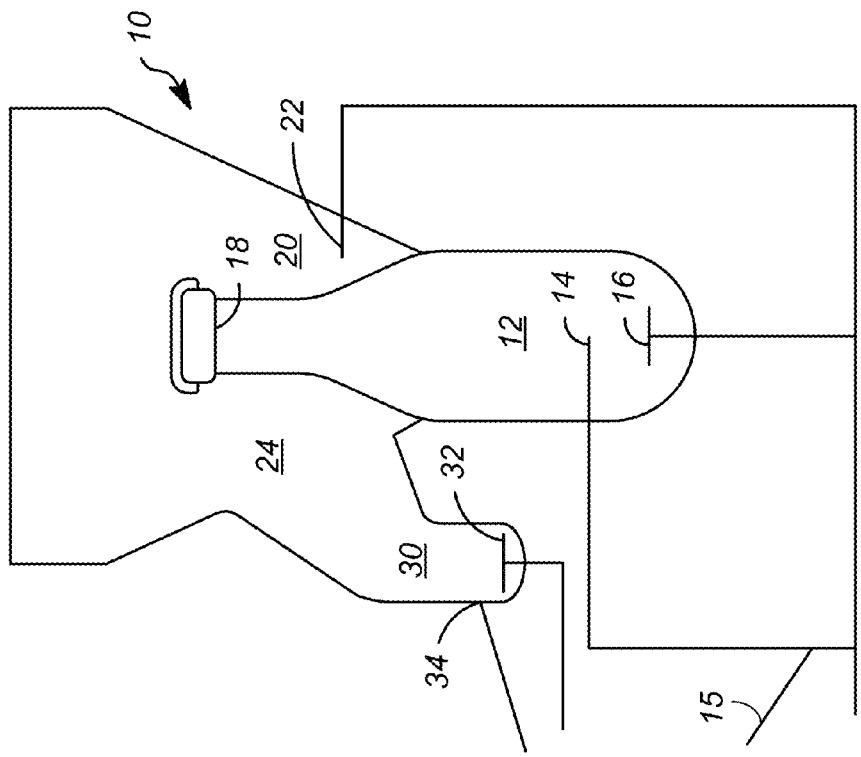
FIG. 1 is a first configuration for performing the catalyst drying.

In this embodiment, the process can be shown in the apparatus of FIG. 1. The apparatus is a regenerator 10 includes a combustion chamber 12, having a catalyst inlet 14 for admitting spent catalyst, a combustion gas inlet 16, and an outlet 18 for conveying catalyst and effluent gas. The apparatus 10 further includes a drying chamber 20, having a drying gas inlet 22, and a catalyst outlet 24. The catalyst from the combustion chamber 12 disengages from the effluent gas as it enters the upper section of the regenerator 10 where the catalyst settles into the drying chamber 20. Drying gas flows over the catalyst and displaces residual combustion gases, and water that has adsorbed onto the catalyst. The catalyst in the drying chamber 20 is in a fluidized bed and flows into a stripping chamber 30. The stripping chamber 30 has a stripping gas inlet 32 and a catalyst outlet 34, where the catalyst is passed to a reactor. The stripping gas can mix with the effluent gases from the combustion chamber 12 and from the drying chamber 20 to be passed out to the atmosphere or other venting means of disposing of the gas. Catalyst is carried to the catalyst inlet 14 through means known in the art, such as a gravity fed pipe 15, where the catalyst is transferred with a lift gas into the combustion chamber 12 through the catalyst inlet 14.

The regenerator 10 can include gas distributors attached to the gas inlets for the different chambers. The gas distributors will facilitate mixing of the catalyst and gases in the respective chambers, and are positioned near the bottom of each respective chamber to minimize or eliminate any zones where the catalyst can collect and sit without passing through the regenerator 10.

The drying gas and combustion gas can be dried air, and can originate from a common source. The air for combustion in the regenerator is supplied by a main air blower, and can be sized to accommodate additional capacity for the dryer 20. A portion of the air for the combustion gas can also be used to lift the catalyst into the combustion chamber 12, entering through the spent catalyst inlet 14.

The drying chamber 20 can comprise a series of trays that can be stacked for distributing and flowing the catalyst across the trays and down the stack. This provides for good contact with drying gas flowing up through the tray stack and contacting the catalyst. The drying gas then mixes with the effluent gas from the combustion chamber 12 and is passed out of the regenerator 10. In an alternate arrangement, the drying chamber 20 can comprise a packing material. The packing material will consist of large open packing objects that allows for the free flow of catalyst down through the packing material, while drying gas flows up through the packing material.

In one embodiment, the drying chamber 20 comprises an annular region around the upper section of the combustion chamber 12. The drying gas is passed through a distributor that distributes the gas around the annular region. The annular bed can be a fluidized bed, or a drying chamber with annular trays or packing.

In another embodiment, the invention comprises a process for drying regenerated catalyst in a continuous catalyst regeneration system. The process includes passing spent catalyst form a dehydrogenation reactor to a regenerator. The catalyst is regenerated in a combustion regeneration process to remove coke deposits on the catalyst, and generates a stream of regenerated catalyst and combustion gas effluent. The regenerated catalyst is separated from the combustion gas, and the regenerated catalyst is passed to a dryer. The dryer is positioned proximate to the combustion chamber gas inlet. The gas for drying the catalyst flows through the dryer, thus drying the catalyst, and passes to the combustion chamber wherein the gas is used to burn the coke off the catalyst. A dried catalyst stream passes to a stripper, and the dried catalyst is contacted with a stripping gas to remove residual oxygen on the catalyst. The stripping gas after flowing over the catalyst is passed to the drying chamber to contribute to the drying of the catalyst. The regenerated, dried and stripped catalyst is then passed to the reactor.

This embodiment is illustrated in the apparatus shown in FIG. 2. The apparatus is a regenerator 110 that includes a combustion chamber 112 with a catalyst inlet 114, a combustion gas inlet 116 and an outlet 118 for carrying catalyst and effluent gas. The apparatus includes a separation chamber 120 in fluid communication with the combustion chamber outlet 118. The separation chamber 120 has a catalyst outlet 122 and an effluent gas outlet. The apparatus further includes a drying chamber 130 with a catalyst inlet 132 in fluid communication with the separation chamber catalyst outlet 122, a catalyst outlet 134, a drying gas inlet 136, and a gas outlet 138 for the dryer effluent gas. The dryer gas outlet 138 is in fluid communication with the combustion chamber 112, and the dryer gas can be used in the combustion process in the combustion chamber 112. The apparatus further includes a stripping chamber 140 having a catalyst inlet 142 in fluid communication with the dryer catalyst outlet 134, a catalyst outlet 144, a stripper gas inlet 146, and an effluent gas outlet in fluid communication with the dryer 130. Catalyst is carried to the catalyst inlet 114 through means known in the art, such as a gravity fed pipe 115, where the catalyst is transferred with a lift gas into the combustion chamber 112 through the catalyst inlet 114.

The gas inlets in the respective chambers can include gas distributors attached to the inlets for distribution of the gas in the respective chambers. The stripping gas which is passed to the dryer, can be passed to a distributor, or passed to the dryer gas inlet and mixed with the drying gas. The drying gas is air and after drying the catalyst is passed to the combustion chamber where it is used in the combustion process. The combustion gas can be passed either entirely through the dryer 130 before being passed to the combustion chamber 112, or can be split with a portion passed through the drying chamber 130 and a portion passed directly to the combustion chamber 112. In this embodiment, a single air source provides the air for combustion and drying, and where the drying air is used in the combustion process without the need for additional air.

In this process, and regenerator design, the drying gas, stripping gas, and combustion chamber flue gases are combined and no additional conduits are required.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. An apparatus for regeneration of catalyst comprising:
   a combustion chamber having a spent dehydrogenation catalyst inlet, a combustion gas inlet, and a combustion chamber outlet for conveying catalyst and effluent gas;
   a drying chamber, having a catalyst/effluent gas inlet in fluid communication with the combustion chamber outlet, where the catalyst separates from the effluent gas, a drying gas inlet, a drying chamber catalyst outlet and a drying chamber effluent gas outlet; and
   a stripping chamber having a catalyst inlet in fluid communication with the drying chamber catalyst outlet, a stripping gas inlet, a stripping chamber catalyst outlet, and a stripping chamber effluent gas outlet; wherein the drying chamber and the stripping chamber are disposed between the combustion chamber catalyst outlet, and a reactor catalyst inlet.

2. The apparatus of claim 1 further comprising a gas distributor attached to the combustion gas inlet for distributing the combustion gas near the bottom of the combustion chamber.

3. The apparatus of claim 1 further comprising a gas distributor attached to the drying gas inlet to distribute the drying gas near the bottom of the drying chamber.

4. The apparatus of claim 1 further comprising a gas distributor attached to the stripping gas inlet to distribute the stripping gas near the bottom of the stripping chamber.

5. The apparatus of claim 1 further comprising an air source in fluid communication with the combustion gas inlet and the drying gas inlet.

6. The apparatus of claim 5 further comprising the air source in fluid communication with the spent catalyst inlet.

7. The apparatus of claim 1 further comprising an air source for carrying the spent catalyst into the combustion chamber.

8. The apparatus of claim 1 further comprising trays disposed within the drying chamber.

9. The apparatus of claim 1 further comprising packing material disposed within the drying chamber.

10. An apparatus for regeneration of catalyst comprising:
    a combustion chamber having a dehydrogenation catalyst inlet, a combustion gas inlet, and a combustion chamber outlet for carrying catalyst and effluent gas;
    a separation chamber having a separation chamber inlet in fluid communication with the combustion chamber outlet, a separation chamber catalyst outlet, and a separation chamber effluent gas outlet;
    a dryer having a catalyst inlet in fluid communication with the separation chamber catalyst outlet, a dryer catalyst outlet, a dryer gas inlet, and a dryer gas outlet, wherein the dryer gas outlet is in fluid communication with the combustor; and
    a stripper, having a catalyst inlet in fluid communication with the dryer catalyst outlet, a catalyst outlet, a stripper gas inlet, and a stripper gas outlet in fluid communication with the dryer gas inlet; wherein the dryer and the stripper are disposed between the combustion chamber catalyst outlet, and a reactor catalyst inlet.

11. The apparatus of claim 10 further comprising a gas distributor attached to the combustion gas inlet for distributing the combustion gas near the bottom of the combustion chamber.

12. The apparatus of claim 10 further comprising a gas distributor attached to the drying gas inlet to distribute the drying gas near the bottom of the drying chamber.

13. The apparatus of claim 10 further comprising a gas distributor attached to the stripping gas inlet to distribute the stripping gas near the bottom of the stripping chamber.

14. The apparatus of claim 10 further comprising an air source in fluid communication with the combustion gas inlet and the drying gas inlet.

15. The apparatus of claim 14 further comprising the air source in fluid communication with the spent catalyst inlet.

16. The apparatus of claim 10 further comprising an air source for carrying the spent catalyst into the combustion chamber.

17. The apparatus of claim 10 further comprising trays disposed within the drying chamber.

18. The apparatus of claim 10 further comprising packing material disposed within the drying chamber.

* * * * *